(12) United States Patent
Sanchez

(10) Patent No.: US 6,732,736 B2
(45) Date of Patent: May 11, 2004

(54) CONDOM WITH APPLICATOR

(76) Inventor: Emilio Rufino Sanchez, Larrea, 1354, Buenos Aires (AR)

( * ) Notice: Subject to any disclaimer, the term of this patent is extended or adjusted under 35 U.S.C. 154(b) by 94 days.

(21) Appl. No.: 10/020,505

(22) Filed: Dec. 12, 2001

(65) Prior Publication Data
US 2002/0121279 A1 Sep. 5, 2002

(30) Foreign Application Priority Data
Dec. 13, 2000 (AR) .................................. P00 01 06601

(51) Int. Cl.[7] .................................................. A61F 6/04
(52) U.S. Cl. ..................................... 128/844; 608/918
(58) Field of Search ............................... 128/842, 844, 128/918; 604/347–353

(56) References Cited

U.S. PATENT DOCUMENTS
4,987,905 A * 1/1991 Broad .......................... 128/844

FOREIGN PATENT DOCUMENTS
| FR | 2649315 | * | 7/1989 |
| FR | 2771923 | * | 12/1997 |
| GB | 2225721 | * | 6/1990 |
| GB | 2361429 | * | 10/2001 |

* cited by examiner

Primary Examiner—Michael A. Brown

(57) ABSTRACT

A condom with applicator for applying the condom over a penis, the condom including a plurality of ribbons having proximal ends fixed to the condom and distal ends removably connected to a ring assembly designed to be manipulated by an user.

14 Claims, 2 Drawing Sheets

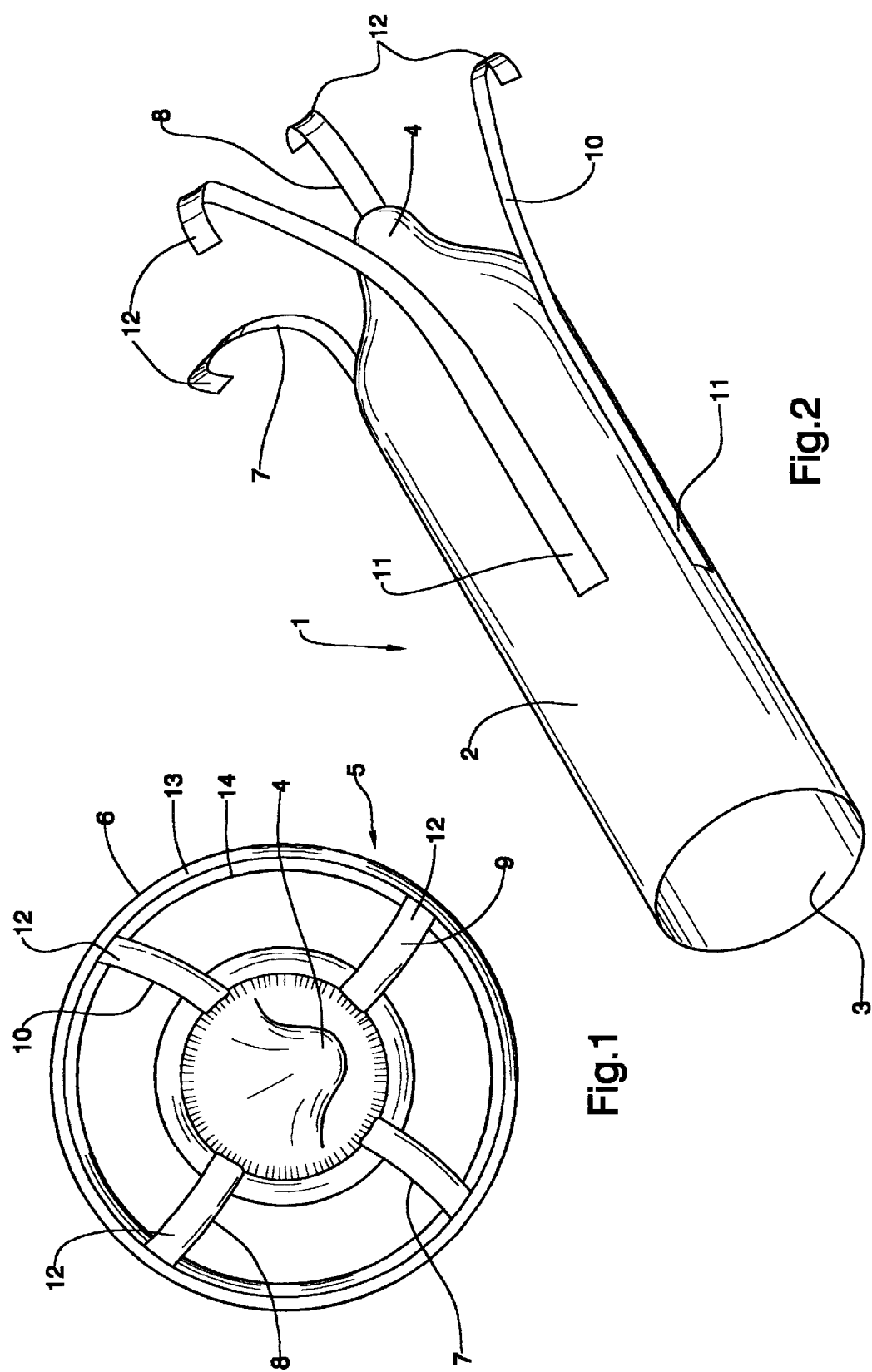

CONDOM WITH APPLICATOR

BACKGROUND OF THE INVENTION

1. Field of the Invention

The present invention relates to a condom with applicator means that is pre-assembled and packaged in conjunction with the condom forming a unit that is ready to be applied over the penis.

2. Description of the Prior Art

Condoms are well known in the art and they comprise a thin walled tubular member made of an impervious resilient expandable material, such as latex or any other appropriate material, having a closed end designed to fit over the glans penis, and an open end for receiving the penis. The condom is packaged and commercialized in a rolled configuration, whereby the thin tubular member is rolled to form a stable disc surrounded by a firm ring. The open end of the tubular member is defined by an annular rib or enlargement providing a better sealing of the condom over the erect penis.

The application of the condom over the penis may be frequently cumbersome depending of several factors including the penis diameter, the resilient material from which the condom is made, the lubricant provided in the condom, etc. Applying the condom is an operation that requires that the disc-shape-rolled condom be placed just over the glans penis and then unrolled over and along the penis with the help of the fingers.

The lubricant used in the condom generally causes the user's fingers to slip off the condom thus making the application troublesome. If the condom is not properly fit over the penis glans when the condom is still unrolled, it is quite difficult to unroll and extend the condom uniformly over the penis. It is frequent to see wrinkles and folding portions in the condom when the condom is not properly unrolled and extended over the penis.

Several applicators have been developed to overcome the above mentioned drawbacks, these systems however have shown to be complex and intricate. Examples o such condom applicators are shown in U.S. Pat. No. 5,471,998 to Kuyumciyan and U.S. Pat. No. 5,549,196 to Kassman.

U.S. Pat. No. 5,471,998 discloses a condom holder for applying the condom onto a penis. The holder being tubular and having a closed end and an open end, whereby the holder may be placed over the penis to cover the upper half of the erect penis. An open end of a condom is mounted into the holder with an unrolled portion of the condom located within the holder. The closed end comprises an air opening and closing means for selectively closing the air opening, with the air opening communicating an air space between the condom and an inner surface of the condom wall with the atmosphere, whereby the air can be withdrawn from the space between the holder and the condom in order to stretch and enlarge the condom for easy placing thereof onto the penis.

U.S. Pat. No. 5,549,196 teaches a packaging including a condom and an applicator that is packaged in a compressed condition into a cap, the applicator having a memory of its original shape whereby, when the applicator is released from the cap, it axially extends under the influence of its memory thus extending the condom over the penis.

While the above holders and applicators have improved the state of the prior art by providing new means for facilitating the applying operation of a condom and obtaining better results, those systems have also shown to be troublesome and complicated to be manipulated and operated.

It would be therefore desirable to find a new system for applying a condom by means of a simple and safety operation but without the need of bulky and complex devices.

Summary of the Invention

It is therefore an object of the present invention to provide a condom having applicator means associated to the condom, with the applicator means being simple and extremely easy to operate.

It is still another object of the present invention to provide a combination of a condom and applicator for guarantying a safety and comfortable application of a condom onto an erect penis, independently of the lubricant conditions of the condom and/or the size of the penis.

It is a further object of the present invention to provide a condom with applicator means for applying the condom over a penis, the condom including a plurality of ribbons having proximal ends fixed to the condom and distal ends connected to a ring assembly designed to be manipulated by an user.

It is still a further object of the present invention to provide a condom for use in an erect penis, the condom comprising a thin-walled tubular member having a closed end and an open end for receiving the penis, the condom being packaged into a rolled configuration, and applicator means comprising a manipulating ring, a plurality of elongated members connected to the manipulating ring, wherein the elongated members are rolled with the condom in a manner that the elongated members remain within the rolled configuration of the condom.

It is even another object of the present invention to provide a condom for use in an erect penis, the condom comprising a thin-walled tubular member having a closed end and an open end for receiving the penis, and applicator means comprising a plurality of elongated flexible members, each flexible member having a proximal portion arranged at the tubular member and a free distal portion longitudinally extending beyond said closed end of the tubular member, and a ring assembly, wherein the free ends of the elongated members are removably fixed to the ring assembly.

The above and other objects, features and advantages of this invention will be better understood when taken in connection with the accompanying drawings and description.

BRIEF DESCRIPTION OF THE DRAWINGS

The present invention is illustrated by way of example in the following drawings wherein:

FIG. 1 shows a plant view from a closed end of a pre-assembled condom and applicator means according to the teachings of the invention;

FIG. 2 shows a perspective view of an unrolled and extended condom of FIG. 1, including the ribbons of the applicator adhered to the condom body, without the manipulating ring being shown;

DESCRIPTION OF THE PREFERRED EMBODIMENTS

Figure 4:
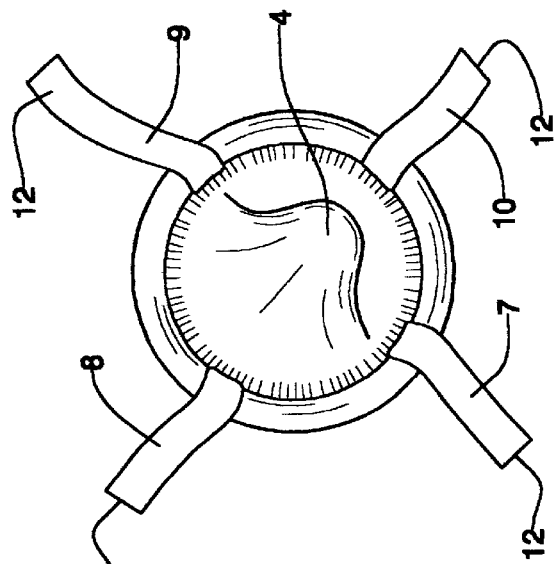
FIG. 4 shows a plant view from the closed end of the condom of FIG. 1, showing the ribbons of the applicator without the manipulating ring.

Now referring in detail to the drawings it may be seen from FIG. 1 and 2, a condom 1 according to the invention, for use in a penis, preferably in an erect penis, wherein the condom comprises a thin wall 2 defining a tubular member. The tubular member has a closed end 4 and an open end 3 having a diameter enough for receiving the penis. The inventive condom is packaged into a rolled configuration, as shown in FIG. 2, and is combined with applicator means 5.

The applicator means comprises a manipulating ring 6 and a plurality of elongated members 7, 8, 9, 10, connected to the manipulating ring. In the packaged condition, FIG. 2, the elongated members are rolled with the condom in a manner that the elongated members remain within the rolled configuration of the condom. Each flexible member 7–10 has a proximal portion indicated with reference 11 for all the elongated members, arranged at the tubular member and a free distal portion 12 longitudinally extending beyond closed end 4 of the condom and connected to ring 6.

Figure 5:
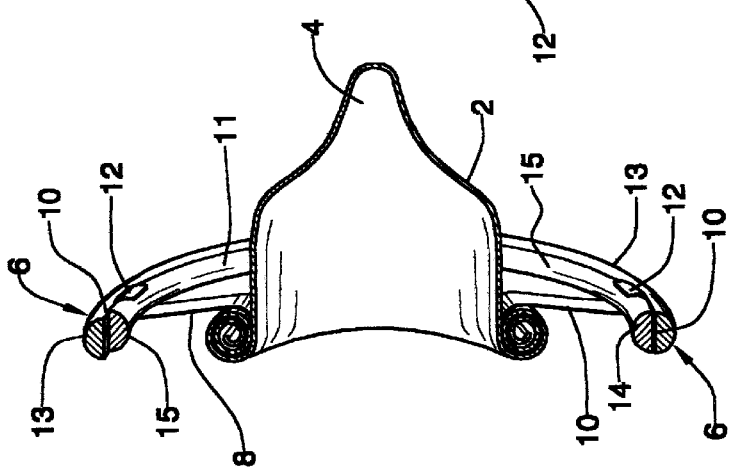
FIG. 5 shows a cross-section of the pre-assembled condom and applicator of FIG. 1.
Figure 3:
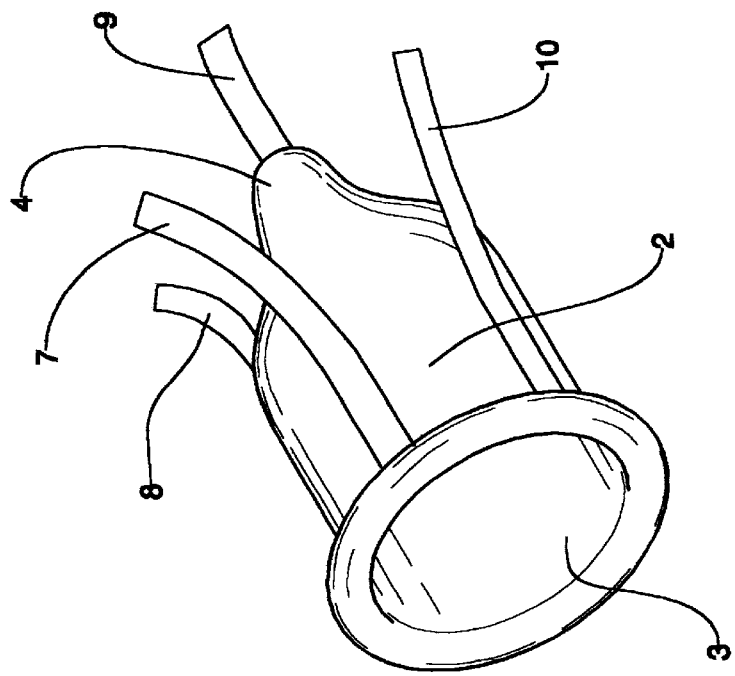
FIG. 3 shows a perspective view of the condom of FIGS. 1 and 2, in a partially unrolled and extended condition, showing the ribbons of the applicator adhered to the condom body.

Ring 6 preferably comprises a ring assembly two coupling rings 13, 14 concentrically arranged, both rings fitting into an adjusted manner, such as by wedging, in a way that the coupling rings tightly fit one over the other. Each elongated member 7–10 preferably comprises a thin ribbon, and each distal portion 12 of each elongated member 7–10 being retained between both coupling rings 13, 14, FIG. 5. Coupling rings 13, 14 are fit together with an interference enough to firmly keep together into the manipulating assembly and retain the distal portions 12 of the ribbons during the storage configuration and when the condom is being unrolled. The coupling rings, however, are fit in a manner that the same can be disassembled by the hands of a user to disassemble rings 13, 14 and remove the rings from the condom before normal use of the condom.

The free ends of the ribbons remains removably fixed and retained between rings 13, 14 and are arranged around the tubular member in a manner that they remain equidistant, that is uniformly spaced apart from each other. The manipulating ring or ring assembly has a diameter enough to pass loosely over penis.

Proximal portions 11 of ribbons 7–10 are arranged in a manner that they remains connected to a portion, preferably a middle portion, of condom 1. Most preferably, the ribbons are connected to the condom and fixed to the condom wall by any bio-compatible adhesive or thermo-welding. Alternatively, ribbons 7–10 are removably connected to condom 1, or, the ribbons may be simply in contact with the condom at the moment the condom is rolled for packaging. In this rolled condition, the ribbons will be retained within the rolled portion of the condom and, when the condom is unrolled, the ribbons will be free to be removed.

In use, the rolled condom is placed with the closed end onto the penis glans and ring 6, taken by the fingers, is pulled down along the penis in order to unroll the condom over the penis length. Once the ring has passed the middle portion of the condom, the condom is practically almost deployed or unrolled and applied over the penis. At this stage, the ring assembly may be disassembled in order to get free from the ribbons. The ribbons may remain in the condom if they are permanently fixed thereto. Otherwise, the ribbons, if simply engaged, or removably connected, to the condom, may be also removed from the condom.

While preferred embodiments of the present invention have been illustrated and described, it will be obvious to those skilled in the art that various changes and modifications may be made therein without departing from the scope of the invention as defined in the appended claims.

I claim:

1. A condom for use on an erect penis, the condom comprising a thin-walled tubular member having a closed end and an open end for receiving the penis, and applicator means comprising:

a plurality of elongated flexible members, each flexible member having a proximal portion arranged at the tubular member and a free distal portion longitudinally extending beyond said closed end of the tubular member, and a manipulating ring assembly, wherein the free distal portions of the elongated members are removably fixed to the ring assembly, and wherein the ring assembly comprises two coupling rings concentrically arranged in a manner that the rings fit tightly together, with said free distal portion of each elongated member being retained between said coupling rings.

2. The condom of claim 1, wherein the proximal portion of each of said elongated members is fixed to the tubular member.

3. The condom of claim 1, wherein the proximal portion of each of said elongated members is removably fixed to the tubular member.

4. The condom of claim 1, wherein each of said elongated members is a ribbon.

5. The condom of claim 1, wherein said two coupling rings are concentrically arranged into a ring assembly and fit together in an interference fit sufficient to keep said rings together and retain said distal portions of said elongated members during storage, with the coupling rings being fit in a manner that they can be disassembled by the hands of a user to remove the coupling rings from the condom before normal use of the condom.

6. The condom of claim 1, wherein the plurality of elongated members are arranged around the tubular member in a manner that they remain uniformly spaced apart from each other.

7. The condom of claim 1, wherein the manipulating ring assembly has a diameter enough to pass loosely over penis.

8. A condom for use on an erect penis, the condom comprising a thin-walled tubular member having a closed end and an open end for receiving the penis, the condom being packaged into a rolled configuration, and applicator means comprising:

a manipulating ring, a plurality of elongated flexible members connected to the manipulating ring, wherein the elongated members are rolled with the condom in a manner that the elongated members remain within the rolled configuration of the condom, wherein each of said elongated flexible members has a proximal portion secured to the tubular member and a free distal portion longitudinally extending beyond said closed end of the tubular member and connected to the ring, wherein the ring comprises a ring assembly, wherein the free distal portions of the flexible elongated members are removably fixed to the ring assembly, and wherein the ring assembly comprises two coupling rings concentrically arranged in a manner that the coupling rings fit tightly together, with the distal portion of each elongated member being retained between said coupling rings.

9. The condom of claim 8, wherein the proximal portion of each elongated flexible member is fixed to the tubular member.

10. The condom of claim 8, wherein the proximal portion of each elongated flexible member is removable fixed to the tubular member.

11. The condom of claim 8, wherein the each elongated flexible member is a ribbon.

12. The condom of claim 8, wherein said two coupling rings are concentrically arranged into a ring assembly and fit together in an interference fit sufficient to keep said rings together and retain the distal portions of the elongated flexible members during storage, with the coupling rings being fit in a manner that they can be disassembled by the hands of a user to remove the rings from the condom before normal use of the condom.

13. The condom of claim 8, wherein the plurality of elongated flexible members are arranged around the tubular member in a manner that they remain uniformly spaced apart from each other.

14. The condom of claim 8, wherein the manipulating ring has a diameter enough to pass loosely over penis.

* * * * *